United States Patent
Kumagai et al.

(10) Patent No.: US 8,730,481 B2
(45) Date of Patent: May 20, 2014

(54) SAGNAC OPTICAL INGREDIENT-MEASURING APPARATUS WITH CIRCULAR POLARIZERS IN PARALLEL

(75) Inventors: Tatsuya Kumagai, Hitachi (JP); Shinji Komatsuzaki, Mito (JP)

(73) Assignee: Hitachi Metals, Ltd., Tokyo (JP)

( * ) Notice: Subject to any disclaimer, the term of this patent is extended or adjusted under 35 U.S.C. 154(b) by 347 days.

(21) Appl. No.: 13/363,927

(22) Filed: Feb. 1, 2012

(65) Prior Publication Data

US 2012/0218555 A1  Aug. 30, 2012

(30) Foreign Application Priority Data

Feb. 24, 2011  (JP) .................................. 2011-038432

(51) Int. Cl.
*G01B 9/02* (2006.01)

(52) U.S. Cl.
USPC ......................................................... 356/483

(58) Field of Classification Search
CPC .................... G01B 2290/70; G01J 2009/0261; G01J 2009/0273; G01D 5/35322; G01N 21/23; G01N 21/22; G01C 19/72
USPC .......................................... 356/460, 483, 480
See application file for complete search history.

(56) References Cited

U.S. PATENT DOCUMENTS

| 7,952,772 B2 * | 5/2011 | Sanders | ........................ 358/480 |
| 7,957,005 B2 * | 6/2011 | Sanders | ........................ 356/483 |

FOREIGN PATENT DOCUMENTS

| JP | 2005-274380 A | 10/2005 |
| JP | 2008-122082 A | 5/2008 |

* cited by examiner

*Primary Examiner* — Hwa Lee
(74) *Attorney, Agent, or Firm* — Robert Mlotkowski Safran & Cole P.C.

(57) ABSTRACT

An optical ingredient-measuring apparatus is provided for measuring a concentration of an optically rotative substance. The apparatus includes a sensor main body which detects a phase difference between linear polarized light beams that propagate through an optical fiber loop in opposite directions, a circular polarized input component interposed in the middle of the optical fiber loop having first and second converters that convert the linear polarized light propagating through the optical fiber loop into left-hand and right-hand circular polarized light, and a concentration detector, installed in the sensor main body, which calculates the concentration of the substance in the sample based on the detected phase difference.

4 Claims, 3 Drawing Sheets

SAGNAC OPTICAL INGREDIENT-MEASURING APPARATUS WITH CIRCULAR POLARIZERS IN PARALLEL

The present application is based on Japanese Patent Application No. 2011-038432 filed on Feb. 24, 2011, the entire contents of which are incorporated herein by reference.

BACKGROUND OF THE INVENTION

1. Field of the Invention

The present invention relates to an optical ingredient-measuring apparatus for optically measuring a concentration of a substance having the optical rotation (optical activity) such as glucose, more particularly, to an optical ingredient-measuring apparatus with the application of a Sagnac interferometric system (interferometer).

2. Related Art

It has been known that the optical rotation (optical activity) of a optically rotative substance such as glucose depends upon the concentration of the substance. Therefore, the sensing of the concentration of such a substance has been carried out by measuring the optical rotation of the substance and calculating the concentration based on the measured optical rotation.

As the method for measuring the optical rotation (or birefringence) of the substance, various kinds of conventional methods such as Senarmont method, orthogonal polarized wave differential method, Muller matrix calculation method, orthogonal polarized wave heterodyne method, modulation phase shift method, wavelength sweep polarization degree measuring method, polarization degree (minimum value) measuring method have been known.

However, since these methods relate to methods for measuring a rotation angle of a plane of polarization (polarization plane) by the optical rotation in a direct manner or with the use of a polarization degree, there are disadvantages in that an angular resolution thereof is low, and that a measurement error is large. Further, there are additional problems in that the measuring apparatus is large-scaled, the elements used for measuring are expensive, the time is needed for adjusting an optical axis, and therefore the measuring apparatus is expensive.

Thus, Japanese Patent Laid-Open No. 2005-274380 (JP-A 2005-274380) proposed an optical ingredient-measuring apparatus with the application of the Sagnac interferometric system that has been used in an optical fiber gyro, etc.

SUMMARY OF THE INVENTION

However, in the optical ingredient-measuring apparatus disclosed by JP-A 2005-274380, since a sample as an object to be measured is inserted in a sensor loop, a phase difference in only one propagation direction is obtained. Therefore, there is a disadvantage in that a sensitivity enough for measuring a glucose concentration in blood cannot be achieved.

Further, in the optical ingredient-measuring apparatus disclosed by JP-A 2005-274380, an optical transmitting part and an optical receiving part are provided for sandwiching the sample to be measured. Therefore, there is a disadvantage that a length of a measuring part is increased and a compact design of the apparatus is difficult.

For solving the aforementioned problems, Japanese Patent Laid-Open No. 2008-122082 (JP-A 2008-122082) proposed a configuration for making the light go (outward) to the sample and return from the sample with the use of a reflection mirror. Nevertheless, it is assumed that the degree of the optical rotation cannot be actually measured by using this apparatus.

More concretely, in the configuration as shown in FIG. 2 of JP-A 2008-122082, an incident light is converted into a circular polarized light by a ¼ wavelength plate 13, then incident on (input to) a sample 8 to be measured via a Faraday rotation optical element 62. At this time, if a right-hand circular polarized light is input to the sample 8 to be measured, the right-hand circular polarized light which transmits through the sample 8 to be measured will be reflected back at a mirror 12, then converted into a left-hand circular polarized light to be again input to the sample 8 to be measured. Assuming that the sample 8 to be measured is a substance which rotates the polarization plane in a clockwise direction such as D-glucose, the right-hand circular polarized light is rotated in the clockwise direction in the going path so that a propagation velocity will become fast, while the left-hand circular polarized light will be rotated in the clockwise direction in the return path so that the propagation velocity will become late. As a result, the phase difference of the returned light with respect to the incident light is not twice but zero. Therefore, it is assumed that the optical rotation cannot be measured by the configuration as shown in FIG. 2 of JP-A 2008-122082.

Therefore, an object of the present invention is to provide an inexpensive and compact optical ingredient-measuring apparatus, by which the high resolution and stable measuring precision can be realized even if the amount of sample is little.

According to a first feature of the invention, an optical ingredient-measuring apparatus for optically measuring a concentration of a substance having optical rotation in a sample as an object to be measured, comprises:

an optical fiber loop;

a sensor main body which converts a light from a light source to a linear polarized light, and divides the linear polarized light to be input to both ends of the optical fiber loop, and detects a phase difference between lights that propagate through the optical fiber loop in opposite directions respectively and are output from the both ends of the optical fiber loop;

a circular polarized light input part, interposed in a middle of the optical fiber loop, which inputs a circular polarized light into the sample, the circular polarized light input part comprising a first optical conversion part which converts the linear polarized light propagating through the optical fiber loop in one direction into a right-hand circular polarized light and inputs the right-hand circular polarized light to the sample, and a second optical conversion part which converts a linear polarized light propagating through the optical fiber loop in an other direction into a left-hand circular polarized light and inputs the left-hand circular polarized light to the sample; and a concentration detecting part, installed in the sensor main body, which calculates the concentration of the substance having the optical rotation in the sample based on the detected phase difference;

in which the first and second optical conversion parts are disposed in parallel at one side of the sample and output the circular polarized lights in the same direction, in which the circular polarized light input part further comprises a reflecting means which reflects back the circular polarized light output from one of the first and second optical conversion parts, makes the light transmit through the sample for at least one round-trip, and thereafter inputs the circular polarized light into an other of the first and second optical conversion parts, in which the reflecting means comprises an even number of reflection mirrors configured to reflect back the input circular polarized light for an even number of times to be output to the sample.

The optical ingredient-measuring apparatus may further comprise delay optical fibers provided in vicinity of the both ends of the optical fiber loop, respectively, in which each of the delay optical fibers comprises an optical fiber constituting the optical fiber loop and including a first portion wound for a predetermined length in one rotating direction and a second portion wound for a same predetermined length as that of the first portion in an other rotating direction.

The optical ingredient-measuring apparatus may further comprise delay optical fibers provided in vicinity of the both ends of the optical fiber loop, respectively, in which each of the delay optical fibers comprises an optical fiber constituting the optical fiber loop, in which one of the delay optical fibers comprises the optical fiber wound for a predetermined length in clockwise direction and an other of the delay optical fibers comprises the optical fiber wound for a same predetermined length as the one of the delay optical fibers in counterclockwise direction.

In the optical ingredient-measuring apparatus, each of the first and second optical conversion parts may comprise a polarized wave rotator which rotates a polarization plane by 45 degrees, and a µ/4 element which converts a linear polarized light into a circular polarized light, in which each of the polarized wave rotator and the $\lambda/4$ element comprises an optical fiber type element, in which a circular polarized light maintaining optical fiber is coupled to the $\lambda/4$ element and the circular polarized light output from the circular polarized light maintaining optical fiber is input into the sample in each of the first and second optical conversion parts.

(Effects of the Invention)

According to the present invention, it is possible to provide an inexpensive and compact optical ingredient-measuring apparatus, by which the high resolution and stable measuring precision can be realized even if the amount of sample is little.

BRIEF DESCRIPTION OF DRAWINGS

Next, embodiments of the present invention will be described in conjunction with appended drawings, wherein.

DETAILED DESCRIPTION OF THE EMBODIMENT

Next, the embodiments of the present invention will be described in more detail in conjunction with appended drawings.

Figure 1:
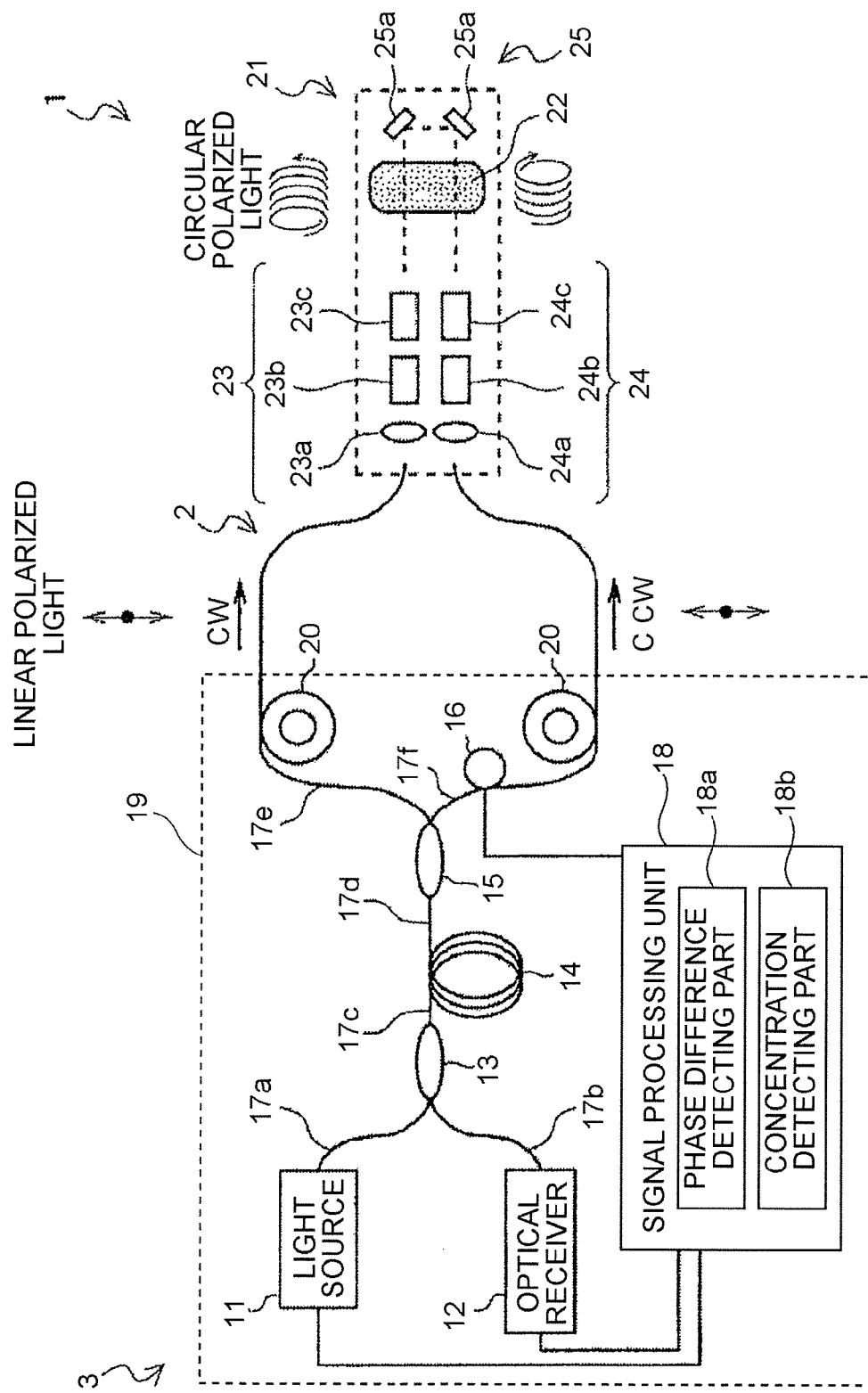
FIG. 1 is a schematic block diagram of an optical ingredient-measuring apparatus in the first embodiment according to the present invention.

FIG. 1 is a schematic block diagram of an optical ingredient-measuring apparatus in the first embodiment according to the present invention.

(An Optical Ingredient-Measuring Apparatus 1)

As shown in FIG. 1, an optical ingredient-measuring apparatus 1 is an apparatus for optically measuring a concentration of a substance having the optical rotation (optical activity) such as glucose, and mainly composed of an optical fiber loop 2, a sensor main body 3 and a circular polarized light input part 21.

The sensor main body 3 converts a light from a light source 11 to a linear polarized light, and divides the linear polarized light to be input to both ends of the optical fiber loop 2, and detects a phase difference between the lights that propagate through the optical fiber loop 2 in opposite directions, respectively, and are output from the both ends of the optical fiber loop 2.

More concretely, the sensor main body 3 comprises the light source 11, an optical receiver 12 such as photodiode, a first optical coupler 13 having three ports 17a to 17c for inputting and outputting the light, a polarizer 14, a second optical coupler 15 having three ports 17d to 17f for inputting and outputting the light, a phase modulator 16, a signal processing unit 18, and a casing 19 for accommodating these parts.

As the light source 11, an SLD (Super Luminescent Diode) is preferably used. By using the SLD, it is possible to reduce an interference noise generated by the interference between a Rayleigh scattering light and a returned light from the optical fiber loop 2. For example, in the case of measuring a blood glucose concentration, it is preferable to choose a light source which emits a light at a near-infrared wavelength for avoiding absorption wavelength bands of water and hemoglobin as the light source 11.

As the first and second optical couplers 13, 15, an optical fiber coupler having 1×2 input/output (I/O) ports as shown in FIG. 1 is used. In addition, as the first and second optical couplers 13, 15, an optical fiber coupler having 2×2 input/output (I/O) ports may be also used.

The first port 17a of the first optical coupler 13 is optically connected to the light source 11, the second port 17b of the first optical coupler 13 is optically connected to the optical receiver 12, and the third port 17c of the first optical coupler 13 is optically connected to one end of the polarizer 14.

The first port 17d of the second optical coupler 15 is optically connected to the other end of the polarizer 14, the second port 17e of the second optical coupler 15 is optically connected to one end of the optical fiber loop 2, and the third port 17f of the second optical coupler 15 is optically connected to the other end of the optical fiber loop 2.

The polarizer 14 is a coil-shaped fiber type polarizer having a core with an increased birefringence, which converts the light from the light source 11 into the linear polarized light.

The phase modulator 16 is installed in the vicinity of the other end of the optical fiber loop 2. The phase modulator 16 is provided for carrying out the phase modulation with a relative time delay on the lights propagating through the optical fiber loop 2 in the opposite directions respectively. A light intensity detected by the optical receiver 12 is proportional to a cosine of the phase difference between the lights propagating through the optical fiber loop 2 in the opposite directions respectively, so that the sensitivity of the sensor for the phase difference around zero, i.e. the sensitivity for little oscillation, is low. Therefore, the phase modulator 16 carries out the phase modulation such that the light intensity detected by the optical receiver 12 is proportional to a sine of the phase difference, thereby the sensitivity for the little oscillation can be improved.

The phase modulator 16 comprises a cylindrical PZT (piezoceramic) as a vibrator, and a part of the optical fiber constituting the optical fiber loop 2 which is wound around the cylindrical PZT. This phase modulator 16 can modulate the phase of the light by expanding and contracting the optical fiber wound around the PZT by applying a voltage to the PZT.

The signal processing unit 18 is provided for driving the light source 11, processing electrical signals generated by photoelectric (optical-electric) conversion of optical signals detected by the optical receiver 12, controlling the modulation level of the phase modulator 16, outputting the processing results (the oscillation waveform, the oscillation intensity, etc.), and the like. The signal processing unit 18 is electrically connected to the light source 11, the optical receiver 12, and the phase modulator 16. The signal processing unit 18 includes a phase difference detecting part 18a which detects a phase difference between the lights that propagate through the optical fiber loop 2 in the opposite directions, respectively, and are output from the both ends of the optical fiber loop 2 based on the electrical signal supplied from the optical receiver 12, and a concentration detecting part 18b to be described below.

The optical fiber loop 2 comprises a polarization plane maintaining optical fiber (PMF: Polarization Maintaining Fiber). For example, in the case of using a single mode optical fiber (SMF: single mode fiber) for the optical fiber loop 2, since two different specific polarization modes that are orthogonal to each other and slightly different in propagation constant propagate through the SMF, the mode conversion occurs by disturbance such as oscillation, temperature change, so that an interference noise due to this mode conversion occurs. For avoiding such an interference noise, the polarization plane maintaining optical fiber (linear polarized light maintaining optical fiber) is used as the optical fiber constituting the optical fiber loop 2.

In the vicinity of the both ends of the optical fiber loop 2 (a region near the second optical coupler 15), delay optical fibers 20, each of which is formed by winding the optical fiber constituting the optical fiber loop 2 (the polarization plane maintaining optical fiber), are provided respectively. The delay optical fibers 20 are accommodated in the casing 19 of the sensor main body 3. Hereinafter, the light propagating through the optical fiber loop 2 in the clockwise direction in FIG. 1 is called as a clockwise light CW, while the light propagating through the optical fiber loop 2 in the counterclockwise direction in FIG. 1 is called as a counterclockwise light CCW.

The delay optical fiber 20 is formed by winding an optical fiber for a predetermined length in one rotating direction, thereafter winding the optical fiber for the same predetermined length in the other rotating direction. This delay optical fiber 20 has both of a function for improving the phase modulation effect by delaying the time that the clockwise light CW reaches the phase modulator 16 with respect to the time that the counterclockwise light CCW reaches the phase modulator 16, and a function of removing a phase difference due to the affect of a rotation of the optical fiber loop 2.

A circular polarized light input part 21 which inputs a circular polarized light into the sample 22 is interposed in the middle of the optical fiber loop 2. It is preferable that the circular polarized light input part 21 is interposed in a center part of the optical fiber loop 2 along its longitudinal direction.

The circular polarized light input part 21 comprises a first optical conversion part 23 which converts the linear polarized light (the clockwise light CW) propagating through the optical fiber loop 2 in one direction into a right-hand circular polarized light and inputs the right-hand circular polarized light to the sample 22 as an object to be measured, and a second optical conversion part 24 which converts the linear polarized light (the counterclockwise light CCW) propagating through the optical fiber loop 2 in the other direction into a left-hand circular polarized light and inputs the left-hand circular polarized light to the sample 22.

The first optical conversion part 23 comprises a lens 23a which converts the linear polarized light (the clockwise light CW) output from the optical fiber loop 2 into a parallel light, a polarized wave rotator 23b to which the parallel light converted from the linear polarized light (the clockwise light CW) by the lens 23a is input, a polarized wave rotator 23b which rotates the polarization plane of the light by 45 degrees, and a λ/4 element 23c which converts the linear polarized light input from the polarized wave rotator 23b into the circular polarized light.

Similarly to the first optical conversion part 23, the second optical conversion part 24 comprises a lens 24a which converts the linear polarized light (the counterclockwise light CCW) output from the optical fiber loop 2 into a parallel light, a polarized wave rotator 24b to which the parallel light converted from the linear polarized light (the counterclockwise light CCW) by the lens 24a is input, a polarized wave rotator 24b which rotates the polarization plane of the light by 45 degrees, and a λ/4 element 24c which converts the linear polarized light from the polarized wave rotator 24b into the circular polarized light.

Here, Faraday rotators are used as the polarized wave rotators 23b, 24b, and ¼ wavelength plates are used as the λ/4 element 23c, 24c.

In this embodiment, both of the first and second optical conversion parts 23, 24 are disposed in parallel (juxtaposed) at one side of the sample 22, to output the circular polarized lights (i.e. the right-hand circular polarized light and the left-hand circular polarized light) in the same direction (the right direction in FIG. 1).

Further, in this embodiment, the circular polarized light input part 21 further comprises a reflecting means 25 which reflects back the circular polarized light output from one optical conversion part 23 (or 24), makes the light transmit through the sample 22 for at least one round-trip (go and return), and thereafter inputs the returned light into the other optical conversion part 24 (or 23). Here, the circular polarized light input part 21 is such configured that the circular polarized light output from one optical conversion part 23 (or 24) and transmitted through the sample 22 is reflected at the reflecting means 25, and input to the sample 22 again, then the circular polarized light transmitted through the sample 22 is input into the other optical conversion part 24 (or 23). In other words, the circular polarized light input part 21 is such configured that the circular polarized light travels for one round-trip through the sample 22. However, the present invention is not limited thereto. The circular polarized light input part 21 may be such configured that the circular polarized light travels for two round-trips through the sample 22. The sensitivity can be improved in accordance with the increase in the number of round-trips.

The reflecting means 25 comprises an even number of reflection mirrors 25a that are configured to reflect back the input circular polarized light for an even number of times to be output to the sample 22. In this embodiment, two reflection mirrors 25a are used such that the input circular polarized light is reflected back for two times to be output to the sample 22.

The optical ingredient-measuring apparatus 1 comprises a concentration detecting part 18b which calculates a concentration of a substance having the optical rotation in the sample 22 (i.e. a concentration of a substance to be measured) based on the phase difference detected by the phase difference detecting part 18*a* of the signal processing unit 18. The concentration detecting part 18*b* is installed in the signal processing unit 18 of the sensor main body 3.

The concentration detecting part 18*b* is configured to detect the concentration of the substance which is the object to be measured, based on the phase difference detected by the phase difference detecting part 18*a* and an analytical curve calculated prior to the measurement. The analytical curve (also called as "standard curve", "calibration curve") expresses a relationship of the concentration of the substance as the object to be measured with respect to the phase difference. The analytical curve is preferably established prior to the actual measurement, by conducting a preliminary experiment with the use of a concentration sample and the like for calibration, and stored as a table or function in a memory of the signal processing unit 18. In addition, it is preferable to carry out the calibration by defining the phase difference in the state that only a sample holder for accommodating the sample 22 is provided, i.e. the state that the sample 22 is not accommodated in the sample holder, as the zero concentration.

(Operation of the Optical Ingredient-Measuring Apparatus 1)

Next, the operation of the optical ingredient-measuring apparatus 1 will be explained below.

At first, the sample 22 is accommodated in the sample holder, and set in the optical ingredient-measuring apparatus 1, then the light is output from the light source 11 in this state. Here, the case of detecting a concentration of the substance which rotates the polarization plane in the clockwise direction such as D-glucose (hereinafter also referred to as "optically rotative substance") in the sample 22 will be explained.

The light output from the light source 11 propagates through the first optical coupler 13, and is converted into the linear polarized light by the polarizer 14, then input to the second optical coupler 15. In the second optical coupler 15, the input light is divided into two, and the divided lights are input into the different ends of the optical fiber loop 2, respectively.

The clockwise light CW input to one end of the optical fiber loop 2 transmits through the delay optical fiber 20 and is input to the first optical conversion part 23. Then, the input light is converted into a parallel light by the lens 23*a*, and the polarization plane thereof is rotated by 45 degrees at the polarized wave rotator 23*b*, and converted into a right-hand circular polarized light by the λ/4 element 23*c*, and finally input to the sample 22. When the right-hand circular polarized light transmits through the sample 22, the right-hand circular polarized light is rotated in the clockwise direction by the optically rotative substance, so that the propagation velocity becomes fast. The right-hand circular polarized light transmitted through the sample 22 is reflected back at a first reflection mirror 25*a* of the reflecting means 25 and converted into a left-hand circular polarized light, then reflected back at a second reflection mirror 25*a* and converted again into the right-hand circular polarized light to be input to the sample 22. When the right-hand circular polarized light transmits through the sample 22, the propagation velocity becomes fast again. The right-hand circular polarized light transmitted through the sample 22 is input to the second optical conversion part 24 and converted into a linear polarized light by the λ/4 element 24*c*. Then, the polarization plane thereof is rotated by 45 degrees at the polarized wave rotator 24*b*, and collected (condensed) by the lens 24*a* to be returned to the optical fiber loop 2. The clockwise light CW returned to the optical fiber loop 2 transmits through the delay optical fiber 20, and is phase-modulated by the phase modulator 16 to be input into the second optical coupler 15.

Similarly, the counterclockwise light CCW input to the other end of the optical fiber loop 2 is phase-modulated by the phase modulator 16, then transmits through the delay optical fiber 20 and is input to the second optical conversion part 24. Then, the input light is converted into a parallel light by the lens 24*a*, and the polarization plane thereof is rotated by 45 degrees at the polarized wave rotator 24*b*, and converted into a left-hand circular polarized light by the λ/4 element 24*c*, and finally input to the sample 22. When the left-hand circular polarized light transmits through the sample 22, the left-hand circular polarized light is rotated in the clockwise direction by the optically rotative substance, so that the propagation velocity becomes late. The left-hand circular polarized light transmitted through the sample 22 is reflected back at the first reflection mirror 25*a* of the reflecting means 25 and converted into a right-hand circular polarized light, then reflected back at the second reflection mirror 25*a* and converted again into the left-hand circular polarized light to be input to the sample 22. When the left-hand circular polarized light transmits through the sample 22, the propagation velocity becomes late again. The left-hand circular polarized light transmitted through the sample 22 is input to the first optical conversion part 23 and converted into a linear polarized light by the λ/4 element 23*c*. Then, the polarization plane is rotated by 45 degrees at the polarized wave rotator 23*b*, and collected (condensed) by the lens 23*a* to return to the optical fiber loop 2. The counterclockwise light CCW returned to the optical fiber loop 2 transmits through the delay optical fiber 20, and is input into the second optical coupler 15.

The clockwise and counterclockwise lights CW, CCW that are input to the second optical coupler 15 interfere with each other in the second optical coupler 15, so that an interference light is generated. This interference light propagates through the polarizer 14 and is divided into two by the first optical coupler 13 again. One of the divided lights is received at the optical receiver 12.

The light received by the optical receiver 12 is converted into an electrical signal, and the electrical signal is input into the signal processing unit 18. The phase difference detecting part 18*a* detects a phase difference between the clockwise light CW and the counterclockwise light CCW based on the input electrical signal, and the concentration detecting part 18*b* detects the concentration of the optically rotative substance in the sample 22 based on the phase difference detected by the phase difference detecting part 18*a*. The detected concentration may be shown by an indicator (not shown), or may be output to a personal computer or the like (not shown).

(Function of the Embodiment)

Next, the function of this embodiment will be explained below.

The optical ingredient-measuring apparatus 1 in this embodiment comprises the circular polarized light input part 21, which is interposed in the middle of the optical fiber loop 2 and comprises the first optical conversion part 23 which converts the linear polarized light (the clockwise light CW) propagating through the optical fiber loop 2 in one direction into a right-hand circular polarized light and inputs the right-hand circular polarized light to the sample 22 as the object to be measured, and the second optical conversion part 24 which converts the linear polarized light (the counterclockwise light CCW) propagating through the optical fiber loop 2 in the other direction into the left-hand circular polarized light and inputs the left-hand circular polarized light to the sample 22. In this embodiment, both of the first and second optical conversion parts 23, 24 are disposed in parallel at the one side of the sample 22, such that the circular polarized lights are output in the same direction. Further, the circular polarized light output from one optical conversion part 23 (or 24) is reflected at the reflecting means, and the light transmits through the sample 22 for at least one round-trip, and thereafter the returned light is input into the other optical conversion part 24 (or 23). The reflecting means 25 comprises the even number of reflection mirrors 25a that are configured to reflect back the input circular polarized light for the even number of times, to be finally output to the sample 22.

According to this configuration, when the circular polarized lights transmits through the sample 22 for the round-trip, the rotating directions of the circular polarized lights can be made the same. For example, if the sample 22 contains a substance which rotates the polarization plane in the clockwise direction such as D-glucose, the propagation velocity of the right-hand circular polarized light, which is the clockwise light CW, becomes fast in both of the going path and the return path, and the propagation velocity of the left-hand circular polarized light, which is the counterclockwise light CCW, becomes late in both of the going path and the return path. Accordingly, it is possible to improve the sensitivity by increasing the phase difference detected by the sensor main body 3. As a result, the high resolution and stable measuring precision can be realized even if the amount of the sample 22 is little.

Figure 2:
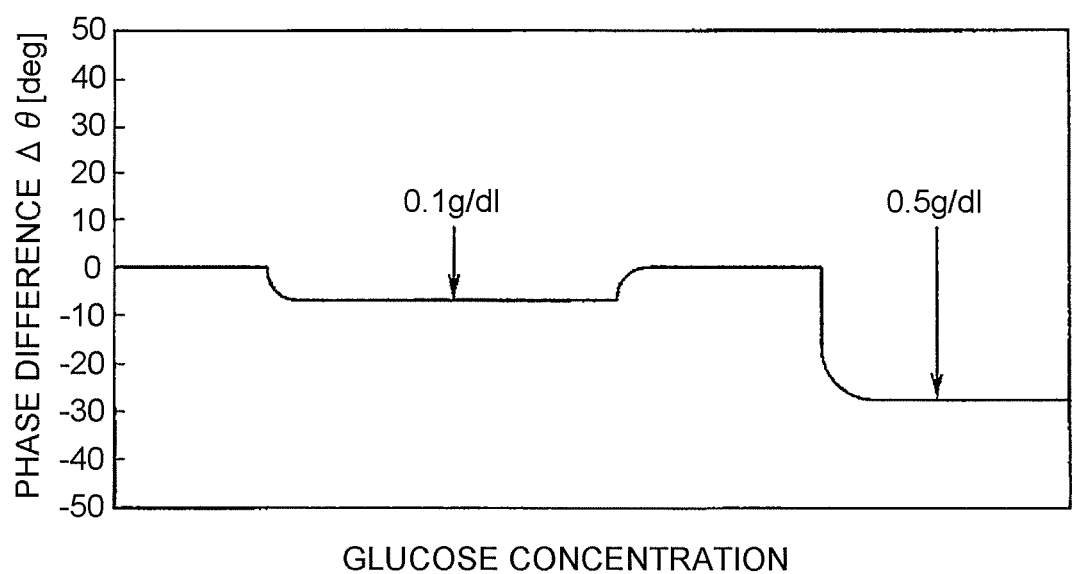
FIG. 2 is a graph showing a relationship between a glucose concentration and a phase difference between a clockwise light and a counterclockwise light when the concentration of glucose is measured by the optical ingredient-measuring apparatus of FIG. 1.

FIG. 2 shows a relationship between a glucose concentration and a phase difference $\Delta\theta$ between the clockwise light CW and the counterclockwise light CCW when the glucose concentration is measured by the optical ingredient-measuring apparatus 1. FIG. 2 shows the phase difference $\Delta\theta$ when the glucose concentration is 0.1 g/dl and 0.5 g/dl as examples. A remarkable phase difference $\Delta\theta$ can be measured, even in the case of the glucose concentration of 0.1 g/dl, which is considered as a slightly high glucose level for a healthy person (physically unimpaired person). Therefore, it is found that the good sensitivity that can cope enough with the measurement of the blood glucose concentration is provided.

Further, according to the optical ingredient-measuring apparatus 1, both of the first and second optical conversion parts 23, 24 are disposed in parallel at the one side of the sample 22 to output the circular polarized lights in the same direction, so that the length of the measuring part can be shortened and the compact design can be realized.

Still further, because the optical ingredient-measuring apparatus 1 is the application of the Sagnac interferometeric system that has been used in the optical fiber gyro, the high resolution and the stable measuring precision can be provided (e.g., a phase difference of 0.001 degrees can be measured easily), and the inexpensive and compact apparatus can be realized. In addition, because the optical ingredient-measuring apparatus 1 is an optical measuring system, there are advantages in that the starting of operation is fast, the measurement time is short, and the real time measuring can be carried out.

In the optical ingredient-measuring apparatus 1, the delay optical fibers 20, each of which is formed by winding the optical fiber constituting the optical fiber loop 2, are provided in the vicinity of the both ends of the optical fiber loop 2, respectively. Each of the delay optical fibers 20 is formed by winding an optical fiber for a predetermined length in the one rotating direction, thereafter winding the optical fiber for the same predetermined length in the other rotating direction. Namely, each of the delay optical fibers 20 comprises an optical fiber constituting the optical fiber loop 2 and including a first portion wound for a predetermined length in one rotating direction and a second portion wound for the same predetermined length as that of the first portion in the other rotating direction. Alternatively, one of the delay optical fibers 20 may be formed by winding the optical fiber for a predetermined length in the clockwise direction, and the other of the delay optical fibers 20 may be formed by winding the optical fiber for the same predetermined length in the counterclockwise direction. Namely, one of the delay optical fibers 20 comprises the optical fiber wound for a predetermined length in the clockwise direction and the other of the delay optical fibers 20 comprises the optical fiber wound for the same predetermined length as the one of the delay optical fibers 20 in counterclockwise direction. According to this configuration, the Sagnac effect can be removed from the measuring result.

Further, in the optical ingredient-measuring apparatus 1, since the sample 22 is located in the middle part (the center part) of the optical fiber loop 2, the clockwise light CW and the counterclockwise light CCW reach at the sample 22 and transmits through the sample 22 at the same time. Therefore, even if the temperature of the sample is varied or a refractive index distribution in the sample is varied, since the clockwise light CW and the counterclockwise light CCW propagate through a medium having the same refractive index (i.e. propagate for the same time period) regardless of the refractive index distribution in the sample caused by the temperature change, the time difference does not occur between the clockwise light CW and the counterclockwise light CCW, so that the measuring result will not be affected by the temperature change of the sample.

(Second Embodiment)

Next, the second embodiment according to the invention will be explained below.

Figure 3:
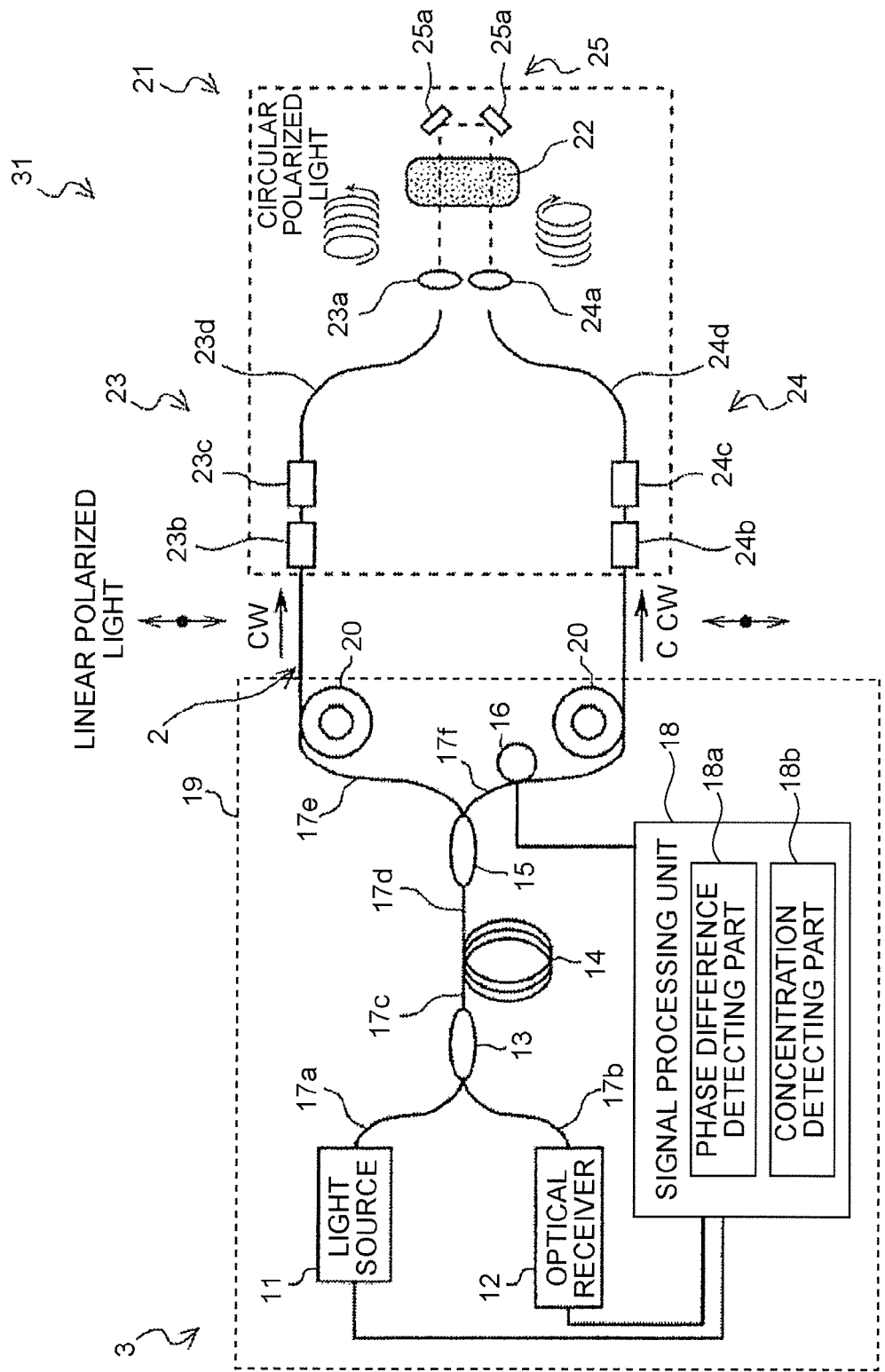
FIG. 3 is a schematic block diagram of an optical ingredient-measuring apparatus in the second embodiment according to the present invention.

FIG. 3 is a schematic block diagram of an optical ingredient-measuring apparatus in the second embodiment according to the present invention.

An optical ingredient-measuring apparatus 31 as shown in FIG. 3 has a basically same configuration as that of the optical ingredient-measuring apparatus 1 as shown in FIG. 1. In the optical ingredient-measuring apparatus 31, both of the first and second optical conversion parts 23, 24 are such configured that each of the polarized wave rotators 23b, 24b and the $\lambda/4$ elements 23c, 24c comprises an optical fiber type element, and the circular polarized light maintaining optical fibers 23d, 24d are coupled to the $\lambda/4$ elements 23c, 24c. Therefore, the circular polarized lights output from the circular polarized light maintaining optical fibers 23d, 24d are converted into parallel lights by the lenses 23a, 24a to be input into the sample 22, respectively.

In the optical ingredient-measuring apparatus 31, as the polarization wave rotators 23b, 24b, it is preferable to use an optical fiber type Faraday rotator having a configuration in that an optical fiber is provided around a perimeter of a conductor which generates a magnetic field when the electric current is flown. Further, as the $\lambda/4$ elements 23c, 24c, it is possible to use a polarization plane maintaining optical fiber in that a portion distant from an output end for about ¼ of a coupling length (wavelength) is fused and twisted by 45 degrees.

According to the optical ingredient-measuring apparatus 31, since each of the polarized wave rotators 23b, 24b and the $\lambda/4$ elements 23c, 24c comprises the optical fiber type element, the influences due to the loss or the reflection of the light can be reduced.

Further, according to the optical ingredient-measuring apparatus 31, it is possible to shorten a distance between the circular polarized light maintaining optical fibers 23d, 24d and the sample 22, so that it is possible to reduce the affect of spreading of a space-propagating light, and to shorten a distance between the first and second optical conversion parts 23, 24 (a distance between the output ends of the circular polarized light maintaining optical fibers 23*d*, 24*d*). Accordingly, the more compact apparatus can be realized.

(Variations)

The present invention is not limited to the aforementioned embodiments, and various modification can be made as long as such a modification does not go beyond the scope of the invention.

For example, in the aforementioned embodiments, the glucose is proposed as the substance which is the object to be measured, however, the present invention is not limited thereto. The concentration of any substance can be measured by the optical ingredient-measuring apparatuses 1, 31 of the present invention as long as such a substance has the optical rotation (optical activity). For example, the optical ingredient-measuring apparatuses 1, 31 of the present invention can be used for measuring a sugar content in fruits and the like.

Although the invention has been described, the invention according to claims is not to be limited by the above-mentioned embodiments and examples. Further, please note that not all combinations of the features described in the embodiments and the examples are not necessary to solve the problem of the invention.

What is claimed is:

1. An optical ingredient-measuring apparatus for optically measuring a concentration of a substance having optical rotation in a sample as an object to be measured, comprising:
   an optical fiber loop;
   a sensor main body which converts a light from a light source to a linear polarized light, and divides the linear polarized light to be input to both ends of the optical fiber loop, and detects a phase difference between lights that propagate through the optical fiber loop in opposite directions respectively and are output from the both ends of the optical fiber loop;
   a circular polarized light input part, in the optical fiber loop, which inputs a circular polarized light into the sample, the circular polarized light input part comprising a first optical conversion part which converts the linear polarized light propagating through the optical fiber loop in one direction into a right-hand circular polarized light and inputs the right-hand circular polarized light to the sample, and a second optical conversion part which converts a linear polarized light propagating through the optical fiber loop in an other direction into a left-hand circular polarized light and inputs the left-hand circular polarized light to the sample; and
   a concentration detecting part, installed in the sensor main body, which calculates the concentration of the substance having the optical rotation in the sample based on the detected phase difference;
   wherein the first and second optical conversion parts are disposed in parallel to each other at one side of the sample and output the circular polarized lights in the same direction,
   wherein the circular polarized light input part further comprises a reflecting means which reflects back the circular polarized light output from one of the first and second optical conversion parts, makes the light transmit through the sample for at least one round-trip, and thereafter inputs the circular polarized light into an other of the first and second optical conversion parts,
   wherein the reflecting means comprises an even number of reflection mirrors configured to reflect back the input circular polarized light for an even number of times to be output to the sample.

2. The optical ingredient-measuring apparatus according to claim 1, further comprising: delay optical fibers provided at both ends of the optical fiber loop, respectively, wherein each of the delay optical fibers comprises an optical fiber constituting the optical fiber loop and including a first portion wound for a predetermined length in one rotating direction and a second portion wound for a same predetermined length as that of the first portion in an other rotating direction.

3. The optical ingredient-measuring apparatus according to claim 1, further comprising: delay optical fibers provided at both ends of the optical fiber loop, respectively, wherein each of the delay optical fibers comprises an optical fiber constituting the optical fiber loop, wherein one of the delay optical fibers comprises the optical fiber wound for a predetermined length in clockwise direction and an other of the delay optical fibers comprises the optical fiber wound for a same predetermined length as the one of the delay optical fibers in counterclockwise direction.

4. The optical ingredient-measuring apparatus according to claim 1, wherein each of the first and second optical conversion parts comprises a polarized wave rotator which rotates a polarization plane by 45 degrees, and a $\lambda/4$ element which converts a linear polarized light into a circular polarized light, wherein each of the polarized wave rotator and the $\lambda/4$ element comprises an optical fiber, wherein a circular polarized light maintaining optical fiber is coupled to the $\lambda/4$ element and the circular polarized light output from the circular polarized light maintaining optical fiber is input into the sample in each of the first and second optical conversion parts.

* * * * *